US00PP30518P2

(12) United States Plant Patent
Pan

(10) Patent No.: US PP30,518 P2
(45) Date of Patent: May 21, 2019

(54) ***CALENDULA* PLANT NAMED 'CDAZ0003'**

(50) Latin Name: *Calendula maritima*
Varietal Denomination: CDAZ0003

(71) Applicant: SYNGENTA PARTICIPATIONS AG, Basel (CH)

(72) Inventor: Shifeng Pan, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,627

(22) Filed: Jul. 10, 2017

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
CPC ..... A01H 5/02
See application file for complete search history.

(56) References Cited

PUBLICATIONS

Syngenta Flowers Cuttings Collection 2017 by Syngetna Flowers; https://issuu.com/syngentaflowers_info/docs/syngentaflowers_cuttingscollection; Feb. 1, 2017; 3 pages.*
magra.com.pl/wp-content/.../Formularz-Etykiety_2018_DYS.xlsx; 2018; 2018; 18 pages.*
Syngenta Flowers 2017-2018 Annuals Assortment Catalog, Published Apr. 2017, 2 pages.
Syngenta Flowers Cuttings Collection 2017, Published on Feb. 1, 2017 , 2 pages.

* cited by examiner

*Primary Examiner* — Kent L Bell
(74) *Attorney, Agent, or Firm* — Dale Skalla

(57) ABSTRACT

A new cultivar of *Calendula* plant named 'CDAZ0003' particularly distinguished by bright yellow flower color, semi-double flower form, and mound spreading plant habit.

1 Drawing Sheet

Latin name of the genus and species of the plant claimed: *Calendula maritima.*
Varietal denomination: 'CDAZ0003'.

BACKGROUND OF THE NEW PLANT

The present invention comprises a new *Calendula*, botanically known as *Calendula maritima*, and hereinafter referred to by the variety name 'CDAZ0003'.

'CDAZ0003' is a product of a planned breeding program. The new cultivar has bright yellow flower color, semi-double flower form, and mound spreading plant habit.

'CDAZ0003' originated from a hybridization made in a greenhouse in June of 2009 in Gilroy, Calif., United States. The female parent was 'GUD0081-4', a plant developed in our breeding program, unpatented, with orange bicolor flower color, fewer branches, and overall larger size than that of 'CDAZ0003'.

The male parent, 'GUD0081-5' was an unpatented, proprietary plant with primrose yellow flower color, is earlier to flower and smaller size than that of 'CDAZ0003'. The resultant seed was sown in January 2010 in a greenhouse in Gilroy, Calif., United States.

'CDAZ0003' was selected as one flowering plant within the progeny of the stated cross in March 2011 in Gilroy, Calif.

The first act of asexual reproduction of 'CDAZ0003' was accomplished when vegetative cuttings were propagated from the initial selection. This initial selection took place on Mar. 15, 2011 in Gilroy, Calif.

BRIEF SUMMARY OF INVENTION

Horticultural examination of plants grown from cuttings of the plant initiated in April, 2012 in Gilroy, Calif., and continuing thereafter, has demonstrated that the combination of characteristics as herein disclosed for 'CDAZ0003' are firmly fixed and are retained through successive generations of asexual reproduction.

'CDAZ0003' has not been observed under all possible environmental conditions. The phenotype may vary significantly with variations in environment such as temperature, light intensity and day length.

A Plant Breeder's Right for this cultivar has not been applied for. 'CDAZ0003' has not been made publicly available prior to the effective filing date of this application, notwithstanding any disclosure that may have been made less than one year prior to the effective filing date of this application by the inventor or another who obtained 'CDAZ0003' directly from the inventor.

The following traits have been repeatedly observed and are determined to be basic characteristics of the new variety. The combination of these characteristics distinguishes this *Calendula* as a new and distinct variety.

BRIEF DESCRIPTION OF THE PHOTOGRAPHS

Figure 1:
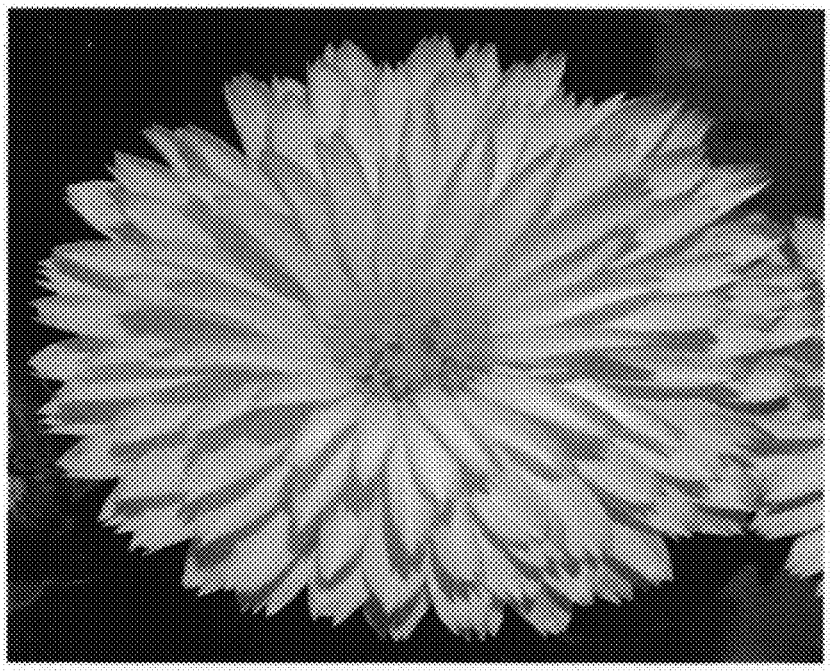
Figure 2:
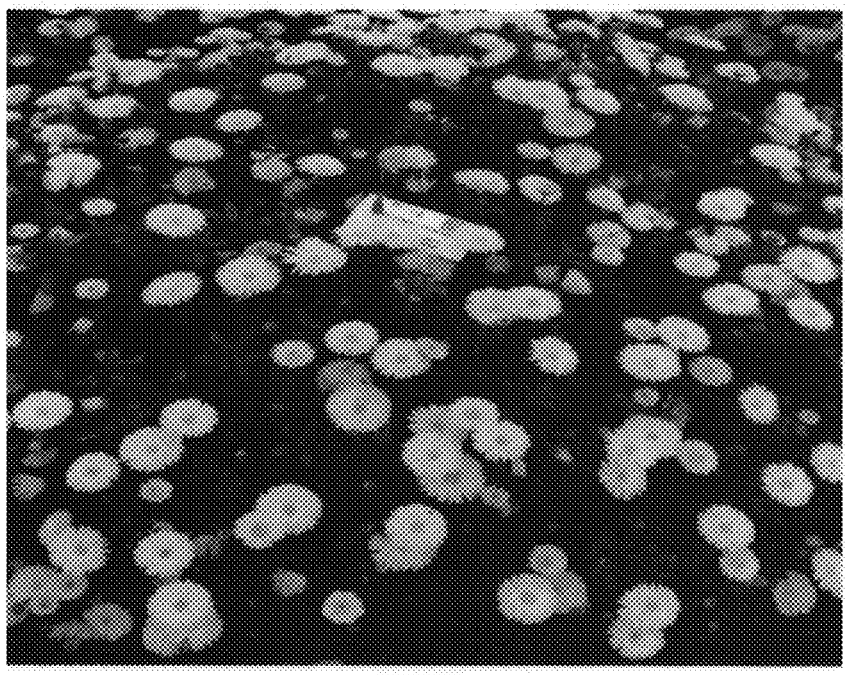

The accompanying photographic drawings show typical flower and foliage characteristics of 'CDAZ0003' with colors being as true as possible with an illustration of this type The photographic drawings show in FIG. 1 a close view of flower of the new variety and in FIG. 2 a flowering plant from an outdoor trial.

The aforementioned photographs: FIG. 1, as well as FIG. 2, were taken in October 2016 both showing a plant from the same natural outdoor trial in Gilroy, Calif. These plants were about 18 weeks of age. One rooted cutting per pot had been planted in a one gallon pot, not pinched in week 22. Plants started flowering end of July.

DETAILED BOTANICAL DESCRIPTION

The measurements were taken in Gilroy, Calif. in May 2017 on the plants from the aforementioned trial.

Color references are made to The Royal Horticultural Society Colour Chart (R.H.S.) 2001.

TABLE 1

DIFFERENCES BETWEEN THE NEW VARIETY 'CDAZ0003' AND A MOST SIMILAR VARIETY

| | 'CDAZ0003' | 'SummerLovers Skyfire Yellow' |
|---|---|---|
| Flower color: | Darker color | Lighter color |
| Flower size: | Bigger flower | Smaller flower |
| Plant habit or size: | Relatively less plant width and more mound plant habit compared to 'SummerLovers Skyfire Yellow' | Relatively wider and therefore less mound plant habit compared to 'CDAZ0003' |
| Frost tolerance: | Frost tolerant | Frost tolerant |
| Flower color: | Darker yellow | Lighter yellow |
| Flower shape: | Semi-Double flower form | Single flower |
| Plant habit or size: | Larger plant size | Smaller plant size |

Plant:

*Form, growth and habit.*—Herbaceous perennial or annual depending on conditions. Compact with strong stems and thick leaves.

*Plant height (above soil).*—22-31 cm.

*Plant height (inflorescence included).*—22-31 cm.

*Plant width.*—80-95 cm.

Roots:

*Number of days to initiate roots.*—About 4 days at about 22 degrees C.

*Number of days to produce a rooted cutting.*—14-16 days at 22 degrees C.

*Type.*—Fine, fibrous, free branching.

*Color.*—RHS N155B but whiter.

Foliage:

*Leaf shape.*—Narrow oblanceolate to narrow oblong.

*Leaf division.*—Simple.

*Leaf base.*—Truncate, decurrent.

*Leaf apex.*—Acuminate.

*Leaf venation.*—Pinnate, color: upper surface; RHS 147D, lower surface; RHS 144B.

*Leaf margins.*—Entire with very short hairs.

*Leaf attachment.*—Sessile.

*Leaf arrangement.*—Alternate.

*Leaf size.*—Length=3.5-3.7 cm, Width=7-10 mm.

*Leaf color.*—Young upper color=RHS NN137A, Young lower color=RHS 137A, Mature upper color=Between RHS 137A and RHS 137B, Mature lower=Between RHS 137B and RHS 137C.

*Leaf surface.*—Upper surface is moderately glossy and slightly rough to the touch, very sparsely covered with very short strigose hairs average of 0.3 mm in length and too small to measure color, lower surface is very slightly glossy and slightly rough to the touch.

*Petioles.*—No petioles present, leaves are decurrent.

Stem:

*Shape.*—Rounded.

*Stem color.*—RHS 137C.

*Stem size.*—Length=25-30 cm, Width=3-5 mm.

*Stem strength.*—Strong and flexible.

*Stem aspect.*—Lateral stems grow in an angle of 45° to the main stem.

*Stem surface.*—Moderately glossy, sparsely covered with very short soft hairs; 0.3 mm in length and too small to measure color.

*Stem number.*—11-13 branches.

*Internode length.*—1.0-3.0 cm.

*Branching.*—Branches grow from base.

Inflorescence:

*Inflorescence type.*—Terminal capitulum consisting of ray florets.

*Inflorescence number.*—Average of 1 per lateral stem.

*Inflorescence fragrance.*—Daisy smell.

*Inflorescence aspect.*—Straight on top of stem.

*Inflorescence longevity.*—A few weeks.

*Inflorescence diameter.*—6 cm.

*Inflorescence height.*—2 cm.

*Inflorescence buds.*—Average of 2 per lateral stem, broad ovate to globular in shape, Length=9-11 mm, Diameter=7-9 mm, Bud color=RHS 2A.

*Receptacle.*—Flattened globular in shape, Color=RHS 145A, Width=3 mm, Length=1 mm.

*Peduncle.*—Length=4.8-5.2 cm, Diameter=2 mm. Color=RHS 138A, terminal peduncle is straight on top of stem, moderate strength, surface is glabrous and slightly glossy and moderately covered with short soft hairs an average of 1 mm in length.

*Involucral bracts.*—Bracts=18-20, Upper color=RHS 137C, Lower color=RHS 137A, Length=7 mm, Width=1 mm, lanceolate in shape, narrowly acute apex, cuneate base, margin entire, upper surface is glabrous, lower surface is densely covered with very short pubescence.

Ray florets:

*Number.*—200-250.

*Arrangement.*—Rotate, 6 whorls.

*Shape.*—Oblanceolate.

*Aspect.*—Slightly upright at the base, held in an average angle of 30°, whole ray floret near horizontal.

*Size.*—Length=1.0-1.3 cm, Width=3.4-3.6 cm.

*Ray floret apex.*—Praemorse.

*Ray floret base.*—Narrow cuneate.

*Ray floret margins.*—Entire.

*Ray floret surface.*—Upper surface is glabrous and velvety, lower surface is slightly glossy and slightly velvety.

*Ray floret color.*—Upper=RHS 2A, Lower=RHS 3B.

*Disc florets.*—~35 disc florets, base RHS 145A, Apex=RHS 14A.

Reproductive organs:

*Gynoecium.*—1 pistil per ray floret, 4 mm in length, stigma unequal decurrent and RHS 165A to RHS 166A color, style is 2 mm in length and RHS 9B in color, ovary RHS 150D in color.

*Androecium.*—No stamens present.

*Fruit and seed.*—N/A.

What is claimed is:

1. A new and distinct variety of *Calendula* plant named 'CDAZ0003' substantially as illustrated and described herein.

* * * * *